(12) United States Patent
Mo (10) Patent No.: US 9,693,970 B2
(45) Date of Patent: *Jul. 4, 2017

(54) TRANSDERMAL DRUG DELIVERY SYSTEM CONTAINING DONEPEZIL

(71) Applicant: NAL Pharmaceuticals Ltd., Hong Kong Sar (HK)

(72) Inventor: Y. Joseph Mo, Princeton, NJ (US)

(73) Assignee: NAL PHARMACEUTICALS GROUP LIMITED, Causeway Bay (HK)

( * ) Notice: Subject to any disclaimer, the term of this patent is extended or adjusted under 35 U.S.C. 154(b) by 0 days.

This patent is subject to a terminal disclaimer.

(21) Appl. No.: 14/825,071

(22) Filed: Aug. 12, 2015

(65) Prior Publication Data

US 2015/0352058 A1    Dec. 10, 2015

Related U.S. Application Data

(63) Continuation of application No. 13/806,565, filed as application No. PCT/KR2011/003052 on Apr. 27, 2011, now Pat. No. 9,155,711.

(30) Foreign Application Priority Data

Jun. 30, 2010   (KR) .................... 10-2010-0062433

(51) Int. Cl.
  *A61K 9/70*     (2006.01)
  *A61K 31/445*   (2006.01)
  *A61K 47/10*    (2017.01)

(52) U.S. Cl.
  CPC .......... *A61K 9/7046* (2013.01); *A61K 9/7061* (2013.01); *A61K 31/445* (2013.01); *A61K 47/10* (2013.01); *A61K 9/7053* (2013.01)

(58) Field of Classification Search
  None
  See application file for complete search history.

(56) References Cited

U.S. PATENT DOCUMENTS

2007/0259028 A1*  11/2007  Ito ................... A61K 9/7084
                                              424/449
2010/0080842 A1*   4/2010  Wen ................. A61K 31/445
                                              424/448
2011/0066120 A1*   3/2011  Lee .................... A61F 13/02
                                              604/290

* cited by examiner

*Primary Examiner* — Jessica Worsham
(74) *Attorney, Agent, or Firm* — Lucas & Mercanti, LLP (57) ABSTRACT

The present invention provides a transdermal drug delivery system comprising a drug-containing matrix layer comprising: (a) donepezil or a pharmaceutically acceptable salt thereof as an active ingredient; and (b) an acrylate-rubber hybrid as an adhesive.

8 Claims, 5 Drawing Sheets

TRANSDERMAL DRUG DELIVERY SYSTEM CONTAINING DONEPEZIL

CROSS REFERENCES TO RELATED APPLICATIONS

This application is a continuation of U.S. patent application Ser. No. 13/806,565, filed Dec. 28, 2012 which is a 371 of PCT/KR2011/003052, filed Apr. 27, 2011, which claims benefit of priority of KR 10-2010-0062433 filed Jun. 30, 2010, the contents of each of which are hereby incorporated by reference in its entirety.

TECHNICAL FIELD

The present invention relates to a transdermal drug delivery system comprising donepezil or a pharmaceutically acceptable salt thereof as an active ingredient, more specifically to a transdermal drug delivery system comprising a drug-containing matrix layer the matrix of which is formed with an acrylate-rubber hybrid adhesive.

BACKGROUND ART

Dementia is a syndrome characterized with complex cognitive disorders, such as memory loss, degeneration of intelligence, personality changes, abnormal behavior, etc. This syndrome is a cerebral degenerative disease, one of the brain diseases in the central nervous system (CNS). In this syndrome, the continuous apoptosis of neural cells inducing degenerative CNS diseases results in irreversible dysfunctions to the neural network, which leads to permanent damages in corresponding functions of the body. The common characteristic of cerebral degenerative diseases is to induce apoptosis of general or specific cells. However, since there is no regenerative potential in differentiated neural cells, the apoptosis of neural cells results in irreversible impairment of the cerebral functions.

From the facts that the causes of dementia are not elucidated completely and that dementia has various etiological and pathophysiological elements, there is no therapeutic agent for dementia that can be used for peculiar administration. However, it has been known that choline acetyltransferase (ChAT) for synthesizing acetylcholine is reduced to about 20 to 30% in the brain of dementia patients. And also, it has been known that the concentration of acetylcholine, one of the neurotransmitter, is reduced by about 16 to 30%. Therefore, researches for using inhibitors against the cholinesterase which hydrolyzes the neurotransmitter, i.e., acetylcholine, have been carried out as an indirect therapy. The cholinesterase has two forms, i.e., acetylcholinesterase (AChE) and butyrylcholinesterase (BuChE). The acetylcholinesterase hydrolyzes acetylcholine, one of the neurotransmitters mediating the parasympathetic nervous system, into choline and acetate. The acetylcholinesterase is formed in the endoplasmic reticulum membrane and then moved to the cytoplasmic membrane to perform its function. The enzyme is distributed mainly in cholinergic nerves and their surroundings, especially in the neuromuscular junctions, although it is also found in plasma, liver and other tissues.

Therefore, most of therapeutic agents currently used in Alzheimer's dementia belong to inhibitors against the acetylcholinesterase (i.e., acetylcholine degrading enzymes), which to include donepezil (ARICEPT™), rivastigmin (EXELON™), galantamine (REMINYL™). Among the acetylcholinesterase inhibitors, donepezil was approved for patients with dementia by the United States Food and Drug Administration (FDA) in 1996, and is being used for treating mild and moderate or more Alzheimer's dementia. Reversible inhibition of donepezil against the acetylcholine degrading enzymes such as acetylcholinesterase and butyrylcholinesterase increases the amount of acetylcholine in the Alzheimer patients' brains in which the amount of acetylcholine was reduced, thereby activating cholinergic neurons.

As a donepezil-containing formulation, there has been used a tablet form which is orally administered to patients suffering from Alzheimer's dementia. However, it has been reported that the oral formulations of donepezil are impossible to avoid hepatic first-pass effect, thereby being easy to affect liver function. And also, it has been reported that the oral formulation of donepezil makes the active ingredient (i.e., donepezil) exist at high concentration in the gastrointestinal tract, thereby causing gastrointestinal side effects.

And also, patients suffering from fairly advanced dementia have difficulty in taking an oral formulation. To solve this problem, Japanese Patent Publication No. 1999-315016 has disclosed an ointment and a suppository for rectal administration. However, these formulations may not be suitable for administering an active ingredient in a sustained manner over a long period of time, through single administration.

U.S. Patent Publication No. 2004/0258741 and Korean Patent Publication Patent No. 10-2005-0037405 have disclosed a transdermal delivery system obtained by using a synthetic rubber polymer such as styrene-isoprene-styrene (SIS) and/or polyisobutylene (PIB). However, since the transdermal delivery system had relatively low skin penetration rate, it was manufactured so as to have very large area, for overcoming the problem. Therefore, patients' compliance may be decreased at the time when the transdermal delivery system is used to patients for 1 to 2 days through single application. In addition, if the drug concentration in the matrix of the transdermal delivery system is more than 8%, a crystalline solid is formed, which may cause decrease of adhesive force, non-uniform skin penetration rate, and storage problems, thereby being difficult to contain the drug therein in a high concentration.

In addition, U.S. Patent Publication Nos. 2010/0080842, 2008/0138388, and 2009/0175929 have disclosed a transdermal delivery system obtained by using an acrylic pressure-sensitive adhesive having a carboxylic acid functional group or hydroxyl functional groups, as well as using a specific absorption enhancer or a specific crystalline donepezil (a Form-B crystal) or a specific crystallization-inhibiting agent (a (meth)acrylate copolymer having a carboxyl group). However, if an acrylic pressure-sensitive adhesive is used as a matrix of the transdermal delivery system, the drug diffusion is slowed in the pressure-sensitive adhesive layer due to the interaction between donepezil and the acrylic polymer in the layer, which also reduce movement of the drug from the pressure-sensitive adhesive layer to the skin. In order to solve this problem, Korean Patent Publication No. 10-2009-0101667 has disclosed a transdermal delivery system obtained by using an EVA (ethylene vinyl acetate) adhesive and a rosin ester resin as a crystallization-inhibiting agent

DISCLOSURE

Technical Problem

The present invention provides a transdermal drug delivery system comprising donepezil or its salt as an active ingredient, which can not only show high skin penetration rate but also continuously maintain a therapeutically effective blood concentration for at least 24 hours. And also, the present invention provides a transdermal drug delivery system, which can inhibit recrystallization of donepezil and maintain skin penetration rate intact, even during the long-term storage.

That is, the present invention provides a donepezil-containing transdermal drug delivery system, both showing high skin penetration rate continuously for more than 24 hours and having an excellent stability.

Technical Solution

In accordance with an aspect of the present invention, there is provided a transdermal drug delivery system comprising a drug-containing matrix layer comprising: (a) donepezil or a pharmaceutically acceptable salt thereof as an active ingredient; and (b) an acrylate-rubber hybrid as an adhesive.

In an embodiment of the present invention, the transdermal drug delivery system may consist of a backing layer, the drug-containing matrix layer, and a release layer.

The acrylate-rubber hybrid may be an acrylic polymer comprising a $C_4$~$C_{18}$ alkyl acrylate monomer grafted with a rubber macromer having a glass transition temperature of not more than −30° C. The acrylate-rubber hybrid adhesive may be present in an amount ranging from 60 to 90% by weight, based on the total weight of the drug-containing matrix layer.

In the transdermal drug delivery system according to the present invention, the donepezil or its pharmaceutically acceptable salt may be present in an amount ranging from 5 to 40% by weight, based on the total weight of the drug-containing matrix layer.

The transdermal drug delivery system according to the present invention may further comprise an acrylate polymer or a methacrylate polymer as a crystallization-inhibiting agent. The crystallization-inhibiting agent may be present in an amount ranging from 1 to 10% by weight, based on the total weight of the drug-containing matrix layer. The crystallization-inhibiting agent may be a copolymer of butyl methacrylate, 2-dimethylaminoethyl methacrylate, and methyl methacrylate in a weight ratio of 1:2:1.

The transdermal drug delivery system according to the present invention may further comprise one or more absorption enhancers selected from the group consisting of terpenes; surfactants; polyoxyethylene alkyl ethers; fatty alcohols; sugar esters; glycerols; alkyl 2-ethyl hexanates; and diethoxylethyl succinates. The absorption enhancer may be present in an amount ranging from 1 to 20% by weight, based on the total weight of the drug-containing matrix layer. The absorption enhancer may be one or more selected from the group consisting of polyethylene glycol palm kernel glyceride, polyoxyethylene lauryl ether, polyglyceryl-3 oleate, lauryl alcohol, and oleyl alcohol.

Advantageous Effects

The transdermal drug delivery system according to the present invention comprises a matrix obtained by using an acrylate-rubber hybrid as an adhesive, which can increase the diffusion rate of donepezil from the matrix layer. Therefore, the transdermal drug delivery system according to the present invention can not only show high skin penetration rate but also continuously maintain a therapeutically effective blood concentration for at least 24 hours. And also, the transdermal drug delivery system of the present invention can inhibit recrystallization of donepezil and maintain skin penetration rate intact, even during the long-term storage.

Therefore, the transdermal drug delivery system according to the present invention can improve drug compliance of patients suffering from Alzheimer's disease.

BEST MODE

As used herein, the term "acrylate-rubber hybrid" adhesive refers to an acrylic polymer grafted with a rubber macromer, including for example the polymer disclosed in U.S. Pat. No. 6,670,417. Preferably, the acrylate-rubber hybrid adhesive may be an acrylic polymer comprising a $C_4$~$C_{18}$ alkyl acrylate monomer grafted with a rubber macromer having a glass transition temperature of not more than −30° C. More preferably, the acrylate-rubber hybrid adhesive may be one or more selected from the commercially available acrylate-rubber hybrids, i.e., DURO-TAK™ 87-502A (National Starch and Chemical company, Bridgewater, N.J., USA), DURO-TAK™ 87-503A (National Starch and Chemical company, Bridgewater, N.J., USA), and DURO-TAK™ 87-504A (National Starch and Chemical company, Bridgewater, N.J., USA).

The present invention provides a transdermal drug delivery system, which comprises a drug-containing matrix layer comprising: (a) donepezil or a pharmaceutically acceptable salt thereof as an active ingredient; and (b) an acrylate-rubber hybrid as an adhesive.

In an embodiment of the present invention, the transdermal drug delivery system may consist of a backing layer, the drug-containing matrix layer, and a release layer.

In the transdermal drug delivery system according to the present invention, the acrylate-rubber hybrid is used as an adhesive; and the acrylate-rubber hybrid adhesive forms a matrix in the drug-containing matrix layer. That is, donepezil or its pharmaceutically acceptable salt is homogeneously dispersed in the acrylate-rubber hybrid adhesive, thereby forming the drug-containing matrix layer.

It is newly found by the present invention that a matrix formed from the acrylate-rubber hybrid having low glass transition temperature can improve flexibility of polymer chains, thereby increasing a diffusion rate of an active ingredient (i.e., donepezil or its pharmaceutically acceptable salt) to the skin from the matrix layer. Therefore, the use of the acrylate-rubber hybrid leads to higher skin penetration rate and excellent adhesive force, in comparison with not only acrylic adhesives having no functional group (for example, DURO-TAK™ 87-4098, DURO-TAK™ 87-900A, DURO-TAK™ 87-9301 etc.) but also other acrylic adhesives having hydroxyl or carboxyl functional group (for example, DURO-TAK™ 87-2516, DURO-TAK™ 87-2510, DURO-TAK™ 87-2525, DURO-TAK™ 87-2596, DURO-TAK™ 87-2825, DURO-TAK™ 87-2502, DURO-TAK™ 87-2979, DURO-TAK™ 87-2074 etc.), all of which are commercially available from National Starch and Chemical Company, Bridgewater, N.J., USA.

The acrylate-rubber hybrid adhesive may be used in an amount sufficient to form a matrix layer, for example, in an amount ranging from 60 to 90% by weight, based on the total weight of the drug-containing matrix layer.

In the transdermal drug delivery system according to the present invention, the donepezil or its pharmaceutically acceptable salt may be used in an amount sufficient to obtain a therapeutically effective blood concentration, for example, in an amount ranging from 5 to 40% by weight, preferably from 10 to 20% by weight, based on the total weight of the drug-containing matrix layer. If the amount of donepezil or its pharmaceutically acceptable salt is more than 40% by weight, drug crystals may be formed in the transdermal drug delivery system, which results in reducing adhesive force or lowering absorption rate of the drug.

The transdermal drug delivery system according to the present invention may further comprise a crystallization-inhibiting agent. The crystallization-inhibiting agent may be an acrylate polymer or a methacrylate polymer, preferably a copolymer of butyl methacrylate, 2-dimethylaminoethyl methacrylate, and methyl methacrylate in a weight ratio of 1:2:1 (for example, EUDRAGIT™ E100). The crystallization-inhibiting agent may be present in an amount ranging from 1 to 10% by weight, based on the total weight of the drug-containing matrix layer.

And also, the transdermal drug delivery system according to the present invention may comprise a conventional absorption enhancer used in the field of a transdermal drug delivery system. The absorption enhancer may be present in an amount ranging from 1 to 20% by weight, preferably from 5 to 15% by weight, based on the total weight of the to drug-containing matrix layer. If the amount of an absorption enhancer is more than 20% by weight, adhesive force may be reduced; or cold flow may occur due to weaken cohesive force.

The absorption enhancer may be one or more selected from the group consisting of terpenes; surfactants; polyoxyethylene alkyl ethers; fatty alcohols; sugar esters; glycerols; alkyl 2-ethyl hexanates; and diethoxylethyl succinates.

Examples of the terpenes include cineole, limonene, etc.

Examples of the surfactants include isopropyl myristate, isopropyl palmitate, 2-(2-ethoxyethoxy) ethanol, oleic acid oleyl ester, caprylocaproyl macrogolglyceride, oleoyl macrogolglyceride, diisopropyl dirrerate, diisopropyl adipate, hexyl laurate, polysorbate, sorbitan oleate, etc.

Examples of the polyoxyethylene alkyl ethers include polyethylene glycol palm kernel glyceride, 2-ethyl hexyl hydroxystearate, polyoxyethylene lauryl ether, polyoxyethylene cetyl ether, etc.

Examples of the fatty alcohols include polyglyceryl-3 oleate, polyethylene glycol almond glyceride, lauryl alcohol, oleyl alcohol, etc.

Examples of the sugar esters include sucrose stearate, sucrose palmitate, sucrose laurate, sucrose behenate, sucrose oleate, sucrose erucate, etc.

Examples of the alkyl 2-ethyl hexanates include 2-ethylhexanonate, cetyl 2-ethylhexanonate, stearyl 2-ethylhexanonate, etc.

Among the above mentioned absorption enhancers, the polyoxyethylene alkyl ethers and/or the fatty alcohols may be preferably used. More preferably, the absorption enhancer may be one or more selected from the group consisting of polyethylene glycol palm kernel glyceride (for example, CROVOL™ A40), polyoxyethylene lauryl ether (for example, BRIJ™ 30, BRIT™ 52, etc.), polyglyceryl-3 oleate (for example, PLUROL OLEIQUE™ CC497), lauryl alcohol, and oleyl alcohol. Most preferably, polyoxyethylene lauryl ether (for example, BRIJ™ 30) may be used as an absorption enhancer.

The transdermal drug delivery system of the present invention may be prepared by forming the drug-containing matrix layer on a release layer and then forming a backing layer thereon. For the release layer, conventional release liners or their laminates used in the field of a transdermal drug delivery system may be used. For example, there may be used a film, a paper, or a laminates thereof, which made of polyethylene, polyester, polyvinyl chloride, polyvinylidene chloride, etc. coated with silicone resin or fluoride resin. And also, drug non-absorbable and flexible materials conventionally used in the field of a transdermal drug to delivery system may be used as the backing layer (also referred to as "backing membrane"). For example, there may be used polyolefin, polyether, a multi-layer ethylene vinyl acetate film, polyester, polyurethane, etc. The transdermal drug delivery system of the present invention may be prepared, for example by dissolving donepezil or its pharmaceutically acceptable salt and an acrylate-rubber hybrid adhesive, optionally along with an absorption enhancer and/or a crystallization-inhibiting agent, in an appropriate solvent (e.g., ethyl acetate, etc.), casting the resulting solution on a release liner coated with silicone followed by drying the mixture, and then laminating a backing layer.

The present invention will be described in further detail with reference to the following examples and experimental examples. These examples and experimental examples are for illustrative purposes only and are not intended to limit the scope of the present invention.

Examples 1 to 11

The transdermal drug delivery systems were prepared according to the components and amounts shown in Table 1. To a mixture of donepezil and an acrylate-rubber hybrid adhesive, optionally along with an absorption enhancer and/or a crystallization-inhibiting agent (EUDRAGIT™ E100), was added ethyl acetate as a solvent so as to attain to 25% of solid content. After stirring each mixture, the resulting each solution was casted on a release liner coated with silicone, followed by drying the mixture. A polyethylene film was laminated onto the resulting each layer to form a backing membrane, so as to prepare each donepezil-containing transdermal drug delivery system.

TABLE 1

| L/I | Component | \% Example (% by weight) | | | | | | | | | | |
|---|---|---|---|---|---|---|---|---|---|---|---|---|
| | | 1 | 2 | 3 | 4 | 5 | 6 | 7 | 8 | 9 | 10 | 11 |
| Active ingredient | Donepezil | 10 | 15 | 15 | 15 | 15 | 15 | 15 | 15 | 35 | 15 | 15 |
| Acrylate-rubber hybrid adhesive | DURO-TAK™ 87-502A | 90 | 85 | 80 | 80 | 80 | 80 | 80 | 75 | 55 | | 74 |
| | DURO-TAK™ 87-503A | | | | | | | | | | 37.5 | |
| | DURO-TAK™ 87-504A | | | | | | | | | | 37.5 | |
| Absorption enhancer | BRIJ™ 30 | | | 5 | | | | | 5 | 5 | 5 | 5 |
| | PLUROL OLEIQUE™ CC497 | | | | 5 | | | | | | | |
| | CROVOL™ A40 | | | | | 5 | | | | | | |
| | Oleyl alcohol | | | | | | 5 | | | | | |
| | Lauryl alcohol | | | | | | | 5 | | | | |
| | BRIJ™ 52 | | | | | | | | | | 5 | |
| Crystallization-inhibiting agent | EUDRAGIT™ E100 | | | | | | | | 5 | 5 | | 6 |

Comparative Examples 1 to 9

The transdermal drug delivery systems were prepared according to the components and amounts shown in Table 2. To a mixture of donepezil and an adhesive, optionally along with an absorption enhancer and/or a crystallization-inhibiting agent (EUDRAGIT™ E100), was added ethyl acetate as a solvent so as to attain to 25% of solid content. After stirring each mixture, the resulting each solution was casted on a release liner coated with silicone, followed by drying the mixture. A polyethylene film was laminated onto the resulting each layer to form a backing membrane, so as to prepare each donepezil-containing transdermal drug delivery system. In case of Comparative Example 6, the release liner coated with fluoride polymer (i.e., SCOTCHPAK™ 1022) was used as a release liner.

TABLE 2

| L/I | Component | Comparative Example (% by weight) | | | | | | | | |
|---|---|---|---|---|---|---|---|---|---|---|
| | | 1 | 2 | 3 | 4 | 5 | 6 | 7 | 8 | 9 |
| Active ingredient | Donepezil | 10 | 10 | 10 | 10 | 10 | 10 | 15 | 35 | 30 |
| Adhesive | Polyisobutylene adhesive (DURO-TAK™ 87-608A) | 90 | | | | | | | | |
| | Styrene-butadiene-styrene adhesive (KRATON™) | | 90 | | | | | | | |
| | Acrylic adhesive having no functional group (DURO-TAK™ 87-4098) | | | 90 | | | | | | |
| | Acrylic adhesive having hydroxyl group (DURO-TAK™ 87-2516) | | | | 90 | | | 75 | 55 | 64 |
| | Acrylic adhesive having carboxyl group (DURO-TAK™ 87-2677) | | | | | 90 | | | | |
| | Silicone adhesive (Silicones in your industry Seach Results DOW CORNING BIO-PSA™ 7-4302) | | | | | | 90 | | | |
| Absorption enhancer | Lauryl alcohol | | | | | | | 5 | 5 | |
| | Palmitic acid | | | | | | | | | 3 |
| | Oleic acid | | | | | | | | | 3 |
| Crystallization-inhibiting agent | EUDRAGIT™ E100 | | | | | | | 5 | 5 | |

Experimental Example 1. Measurement of Skin Penetration Rate of the Transdermal Drug Delivery Compositions According to Adhesives The transdermal drug delivery systems prepared in Example 1 and Comparative Examples 1 to 6 were applied onto hairless mouse skins, for determining their skin penetration rates. Specifically, skins were excised from hairless mice (6 to 8 weeks old) right before the experiment. Each transdermal drug delivery system was cut in a circular form having a size of 2 cm$^2$ and then attached to the isolated skins. Each resulting skin was fixed in each flow-through diffusion cell with a clamp thereof. To the receiver thereof, was added an isotonic phosphate buffer solution (pH 6.0). While the diffusion cell was maintained at 37° C. under stirring with a magnetic stirrer, samples were collected at an interval of 4 hours for 24 hours. The samples were subject to quantitative analysis using high-performance liquid chromatography under the following conditions.

TABLE 3

| Column | C-18 (Gemini, 10 cm, 5 µm) |
|---|---|
| Mobile phase | Acetonitrile/phosphate buffer (pH 2.7) = 70/30 |
| Flow rate | 1 ml/min |
| Wavelength | 315 nm |
| Temperature | 30° C. |

Figure 1:
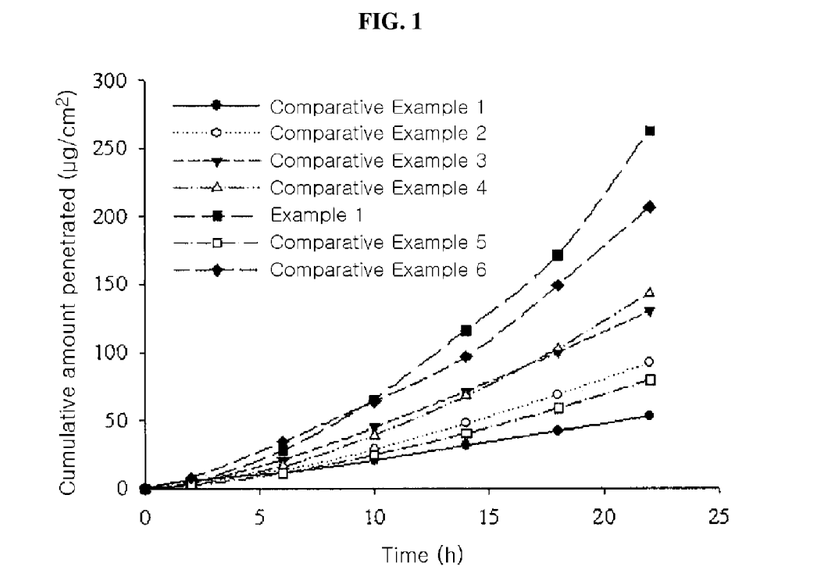
FIG. 1 shows the results obtained by measuring skin penetration rates of the transdermal drug delivery systems according to adhesives.

FIG. 1 shows the results obtained by measuring skin penetration rates as in the above. From the results shown in FIG. 1, it can be seen that the transdermal drug delivery system obtained by using acrylate-rubber hybrid adhesive according to the present invention showed remarkably increased skin penetration rate, in comparison with those obtained by using other adhesives. The transdermal drug delivery system of Comparative Example 6 in which a silicone adhesive was used showed relatively higher skin penetration rate than those in which acrylic adhesives were used; but the penetration rate thereof was decreased with the lapse of time. However, the transdermal drug delivery system of Example 1 showed significant higher skin penetration rate than that of Comparative Example 6; and the penetration rate thereof was more increased with the lapse of time.

Figure 2:
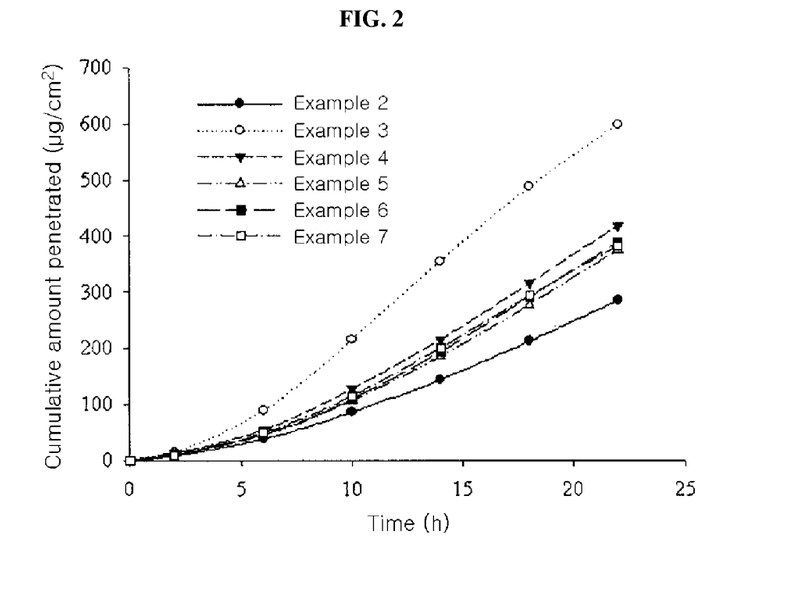
FIG. 2 shows the results obtained by measuring skin penetration rates of the transdermal drug delivery systems according to absorption enhancers.

Experimental Example 2. Measurement of Skin Penetration Rate of the Transdermal Drug Delivery Systems According to Absorption Enhancers Skin penetration rates of the transdermal drug delivery systems prepared in Examples 2 to 7 were determined according to the same methods as in Experimental Example 1. The results thereof were shown in FIG. 2. From the results shown in FIG. 2, it can be seen that the transdermal drug delivery systems of Examples 3 to 7 comprising an absorption enhancer showed more excellent skin penetration rate than that of Example 2 having no absorption enhancer. Especially, the transdermal drug delivery system of Example 3, which comprises polyoxyethylene lauryl ether (for example, BRIJ™ 30) as an absorption enhancer, showed most excellent skin penetration rate.

Experimental Example 3. Comparative Study of Skin Penetration Rate (1)

Skin penetration rates of the transdermal drug delivery systems according to US Patent Publication No. 2008/0138388 (Comparative Examples 7 and 8) and the transdermal drug delivery systems of the present invention (Examples 8 and 9) were determined according to the same methods as in Experimental Example 1. The results thereof were shown in FIG. 3.

Figure 3:
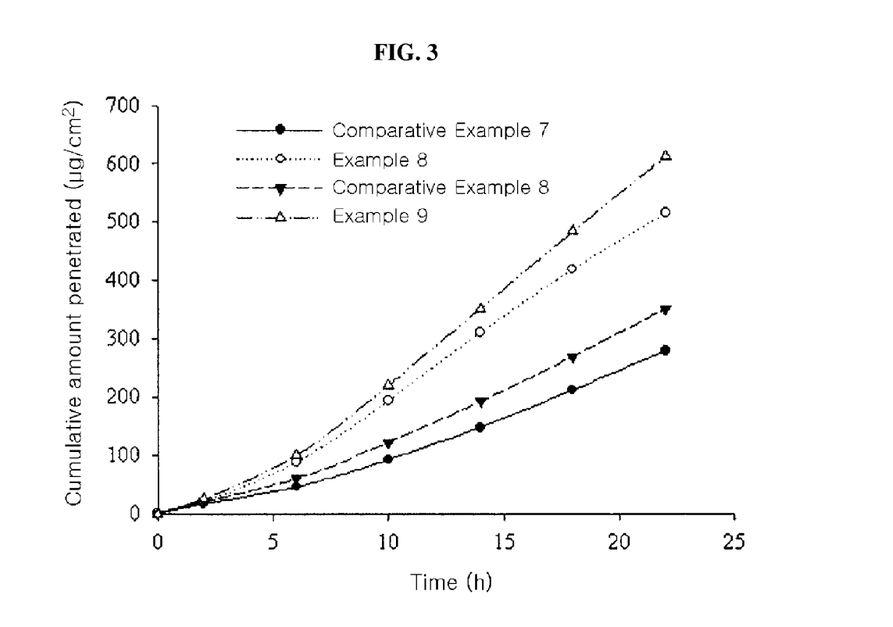
FIG. 3 shows the results obtained by comparing skin penetration rates of the transdermal drug delivery systems prepared according to the present invention and according to the prior art (US Patent Publication No. 2008/0138388), respectively.

From the results shown in FIG. 3, it can be seen that the transdermal drug delivery systems according to the present invention showed higher skin penetration rate than those of Comparative Examples 7 and 8. Especially, although the transdermal drug delivery system of Example 8 comprises donepezil in a lower amount than that of Comparative Example 8, the transdermal drug delivery system of Example 8 showed remarkably high skin penetration rate.

Experimental Example 4. Comparative Study of Skin Penetration Rate (2)

Skin penetration rates of the transdermal drug delivery system according to US Patent Publication No. 2009/0175929 (Comparative Example 9) and the transdermal drug delivery system of the present invention (Example 10) were determined according to the same methods as in Experimental Example 1. The results thereof were shown in FIG. 4.

Figure 4:
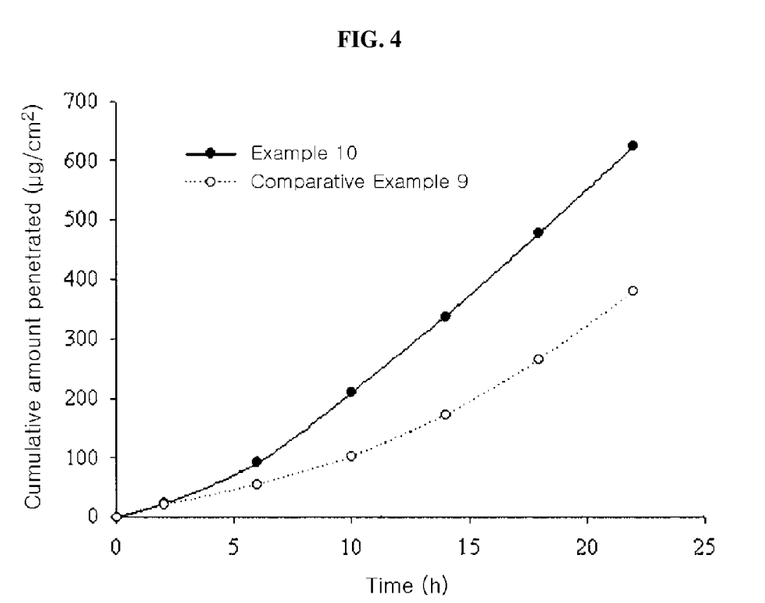
FIG. 4 shows the results obtained by comparing skin penetration rates of the transdermal drug delivery systems prepared according to the present invention and according to the prior art (US Patent Publication No. 2009/0175929), respectively.

From the results shown in FIG. 4, it can be seen that the transdermal drug delivery system according to the present invention showed higher skin penetration rate than that of Comparative Example 9. Especially, although the transdermal drug delivery system of Example 10 comprises donepezil in a lower amount than that of Comparative Example 9, the transdermal drug delivery system of Example 10 showed remarkably high skin penetration rate.

Figure 5:
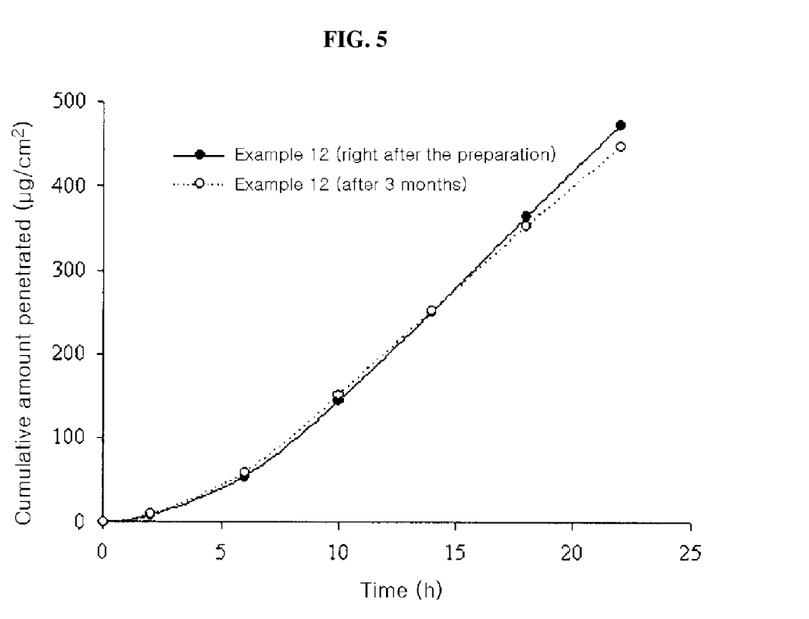
FIG. 5 shows the results obtained by measuring skin penetration rates of the transdermal drug delivery system according to storage period.

Experimental Example 5. Measurement of Skin Penetration Rate of the Transdermal Drug Delivery System According to Storage Period We determined skin penetration rates of the transdermal drug delivery system of Example 11 right after the preparation thereof and after the storage thereof at room temperature for 3 months, according to the same methods as in Experimental Example 1. The results thereof were shown in FIG. 5. From the results shown in FIG. 5, it can be seen that the skin penetration rates of the both samples were the same. And also, as a result of observation with naked eyes, no donepezil crystal was formed in the sample after the storage for 3 months.

I claim:
1. A transdermal drug delivery system comprising:
    a backing layer;
    a drug-containing matrix layer; and
    a release layer,
wherein the drug-containing matrix layer comprises:
    (a) donepezil or a pharmaceutically acceptable salt thereof as an active ingredient;
    (b) an acrylate-rubber hybrid as an adhesive;
    (c) an absorption enhancer; and
    (d) a crystallization-inhibiting agent,
wherein:
    the transdermal drug delivery system has an increased skin penetration rate;
    donepezil or its pharmaceutically acceptable salt is in an amount of 10 to 20% by weight of the total weight of the drug-containing matrix layer;
    the absorption enhancer is in an amount of 5 to 15% by weight of the total weight of the drug-containing matrix layer; and the crystallization-inhibiting agent is in an amount of 1 to 10% by weight of the total weight of the drug-containing matrix layer.

2. The transdermal drug delivery system of claim 1, wherein the acrylate-rubber hybrid is an acrylic polymer comprising a $C_4$~$C_{18}$ alkyl acrylate monomer grafted with a rubber macromer having a glass transition temperature of not more than −30° C.

3. The transdermal drug delivery system of claim 1, wherein the acrylate-rubber hybrid is present in an amount ranging from 60 to 90% by weight, based on the total weight of the drug-containing matrix layer.

4. The transdermal drug delivery system of claim 1, wherein the crystallization-inhibiting agent is an acrylate polymer or a methacrylate polymer.

5. The transdermal drug delivery system of claim 1, wherein the crystallization-inhibiting agent is a copolymer of butyl methacrylate, 2-dimethylaminoethyl methacrylate, and methyl methacrylate in a weight ratio of 1:2:1.

6. The transdermal drug delivery system of claim 1, wherein the absorption enhancer is selected from the group consisting of terpenes, surfactants, polyoxyethylene alkyl ethers, fatty alcohols, sugar esters, glycerols, alkyl 2-ethyl hexanates, and diethoxyethyl succinates.

7. The transdermal drug delivery system of claim 1, wherein the absorption enhancer is present in an amount of 5% by weight, based on the total weight of the drug-containing matrix layer.

8. The transdermal drug delivery system of claim 1, wherein the absorption enhancer is polyethylene glycol palm kernel glyceride, polyoxyethylene lauryl ether, polyglyceryl-3 oleate, lauryl alcohol, oleyl alcohol, or a mixture thereof.

\* \* \* \* \*